United States Patent [19]
Duncan et al.

[11] Patent Number: 5,882,352
[45] Date of Patent: Mar. 16, 1999

[54] AUTOMATIC ADJUSTMENT OF DETECTION RATE THRESHOLD IN AN IMPLANTABLE ANTITACHYCARDIA THERAPY DEVICE

[75] Inventors: James L. Duncan, Alpharetta, Ga.; Bruce Wilkoff, Cleveland, Ohio; James D. Causey, III, Simi Valley, Calif.

[73] Assignee: Pacesetter, Inc., Sylmar, Calif.

[21] Appl. No.: 449,970

[22] Filed: May 25, 1995

[51] Int. Cl.⁶ .................................................. A61N 1/365
[52] U.S. Cl. .................................. 607/4; 607/14; 607/18; 607/19
[58] Field of Search .............................. 607/4, 5, 6, 14, 607/17–19; 128/706, 705

[56] References Cited

U.S. PATENT DOCUMENTS

| | | | |
|---|---|---|---|
| 3,942,534 | 3/1976 | Allen et al. | 128/419 |
| 4,422,459 | 12/1983 | Simson | 128/702 |
| 4,428,378 | 1/1984 | Anderson et al. | 128/419 |
| 4,554,920 | 11/1985 | Baker et al. | 128/419 |
| 4,574,437 | 3/1986 | Segerstad et al. | 128/419 |
| 4,576,183 | 3/1986 | Plicchi et al. | 128/723 |
| 4,712,555 | 12/1987 | Thornander | 128/419 |
| 4,712,556 | 12/1987 | Baker | 128/419 |
| 4,771,780 | 9/1988 | Sholder | 128/419 |
| 4,787,389 | 11/1988 | Tarjan | 128/419 |
| 4,788,980 | 12/1988 | Mann et al. | 128/419 |
| 4,846,195 | 7/1989 | Alt | 128/782 |
| 4,940,052 | 7/1990 | Mann et al. | 128/419 |
| 4,940,053 | 7/1990 | Mann et al. | 128/419 |
| 4,989,602 | 2/1991 | Sholder et al. | 128/419 |
| 5,074,308 | 12/1991 | Sholder et al. | 128/697 |
| 5,103,822 | 4/1992 | Duncan | 128/419 |

Primary Examiner—William E. Kamm
Assistant Examiner—Kennedy J. Schaetzle

[57] ABSTRACT

An antitachycardia stimulation device that automatically adjusts its detection rate threshold as a function of a sensed physiological parameter indicative of cardiac rate. The implantable antitachycardia stimulation device includes heart rate detection circuitry and antitachycardia therapy circuitry for applying a specific antitachycardia therapy in the event that the detected heart rate falls within at least one tachycardia rate zone. The tachycardia rate zone is defined by a lower threshold limit, and may also be defined by an upper threshold limit if more than one rate zone is used. The lower threshold limit is automatically adjusted as a function of an independently sensed physiological parameter that predicts a normal or natural change in the heart rate. If more then one rate zone is used, other threshold limits may also be adjusted automatically as a separate function of the same sensed physiological parameter. In one embodiment of the invention, the implantable stimulation device comprises a rate-responsive pacemaker, and the sensed physiological parameter used to adjust the rate threshold limit(s) is also used to define a sensor indicated rate signal to control the pacing rate of the pacemaker.

39 Claims, 4 Drawing Sheets

AUTOMATIC ADJUSTMENT OF DETECTION RATE THRESHOLD IN AN IMPLANTABLE ANTITACHYCARDIA THERAPY DEVICE

FIELD OF THE INVENTION

The present invention relates to implantable medical devices and methods, and more particularly to an implantable antitachycardia device, e.g., an antitachycardia pacemaker or defibrillator-cardioverter, that automatically adjusts its detection rate threshold as a function of the sensed cardiac rate.

BACKGROUND OF THE INVENTION

Antitachycardia therapy devices, such a antitachycardia pacemakers or antitachycardia defibrillators-cardioverters, utilize heart rate detection circuitry to determine the onset of a cardiac arrhythmia. Such rate detection circuitry typically includes discrete rate zones for the classification of arrhythmias. The rate zones, which are typically set through one or more user programmable parameters, dictate what type of device response, i.e., what type of antitachycardia therapy, will be provided whenever the detected heart rate falls within a given rate zone. For example, a user may define a low rate ventricular tachycardia zone which is identified by a low rate limit, rate A (e.g., 135 bpm), and a high rate limit, rate B (e.g., 175 bpm). Any detected heart rate that falls within this zone would thus be identified as a low rate ventricular tachycardia, and such identification would trigger an appropriate therapy from the antitachycardia therapy device. Similarly, a high rate tachycardia classification zone, e.g., between 175 and 240 bpm, may be defined that borders the low rate tachycardia zone. Thus, any detected heart rate that falls within the high rate tachycardia zone would be identified as a high rate ventricular tachycardia, thereby triggering another type of therapy from the antitachycardia therapy device. Further, in some devices, a third zone may be added just above the high rate tachycardia zone. Hence, in this fashion, the user can set up a single large rate zone or as may smaller bordering rate zones as desired, with each rate zone providing a particular one of a variety of independent antitachycardia therapies that is automatically applied by the device in order to terminate a perceived arrhythmia. As needed, the detection and classification of arrhythmias may be further based on additional parameters, in addition to heart rate, such as the hemodynamics identified by a particular sensor, and/or other rate parameters, such as the onset, stability or duration of the detected heart rate.

Unfortunately, the selection of discrete rate zones may prove to be problematic when a patient has a normal sinus rate that enters into one of the tachycardia zones during exercise or during other periods of physiological stress. Although various discriminating parameters, such as the onset and stability of the detected rate or rhythm, may be used in an attempt to minimize the detection of a fast normal sinus rate as a tachycardia rate, the fast rhythm or rate may still be incorrectly classified as an arrhythmia, resulting in antitachycardia therapy being provided by the device. Such antitachycardia therapy could be inappropriate, and even dangerous, because it may actually induce an actual arrhythmia when provided incorrectly.

Hence, it is apparent that there is a critical need for rate detection circuitry in an antitachyardia pacemaker or defibrillator-cardioverter that minimizes the risk of incorrectly identifying and classifying a fast sinus rate (for which antitachycardia therapy is not needed nor desired) as an arrhythmia (for which antitachycardia therapy is needed and desired).

SUMMARY OF THE INVENTION

Accordingly, it is a general feature of the invention to provide rate detection circuitry in an implantable antitachycardia pacemaker or ICD that minimizes the risk of incorrectly identifying and classifying a fast sinus rate as an arrhythmia for which antitachycardia therapy is invoked.

Yet a further feature of the invention is to provide an implantable antitachycardia device that automatically adjusts its detection rate zone(s), e.g., by automatically adjusting the lower and/or upper limits of such rate zone(s), as a function of a sensed physiologic parameter of the patient, such a physical activity, which physiologic parameter provides an indication whether the sinus heart rate is expected to change.

An additional feature of the invention is to provide an implantable rate-responsive antitachycardia pacemaker wherein a raw signal from a physiologic sensor used with the pacemaker independently provides: (1) the basis for deriving a sensor indicated rate (SIR) signal that sets the pacing rate of the pacemaker, and (2) the basis for adjusting the lower and/or upper limits of a detection rate zone(s) used by the pacemaker to detect when an arrhythmia (for which antitachycardia therapy is needed) is present.

In accordance with one aspect of the invention, an implantable antitachycardia medical device includes: (1) heart rate detection circuitry, (2) antitachycardia therapy circuitry, and (3) a physiologic sensor and associated sensor processing circuitry. The antitachycardia therapy circuitry applies a specific antitachycardia therapy in the event that the heart rate, as detected by the heart rate detection circuitry, falls within at least one tachycardia rate zone. The tachycardia rate zone is defined by a lower threshold limit, and may also be defined by an upper threshold limit if more than one rate zone is used.

Advantageously, in accordance with the invention, at least the lower threshold limit of the rate zone is automatically adjusted as a function of an independently sensed physiological parameter, e.g., physical activity, that is sensed by the physiologic sensor. The physiological parameter predicts a normal or natural change in the heart rate. If more than one rate zone is used, then the other threshold limits, e.g., the upper threshold limit, may also be adjusted automatically as a separate function of the same sensed physiological parameter, or a different physiological parameter, thereby causing the entire tachycardia rate zone to change as a function of the sensed physiological parameter.

In accordance with another aspect of the invention, the implantable medical device comprises a rate-responsive pacemaker, and the sensed physiological parameter used to adjust the rate threshold limit(s) of the rate-responsive pacemaker is also used to define a sensor indicated rate signal used to define the pacing rate of the rate-responsive pacemaker. However, in such instance the sensor signal is independently processed so that the rate threshold limit(s) varies as a first independent function of the sensor signal, and the sensor indicated rate varies as a second independent function of the sensor signal.

In accordance with still another aspect of the invention, a rate-responsive pacemaker is coupled to an ICD, as taught, e.g., in U.S. Pat. No. 4,989,602, and the rate threshold limit(s) of the pacemaker and/or ICD are automatically adjusted as a function of sensed physiologic parameter, such as physical activity, that is sensed by the sensor of the rate-responsive pacemaker, and/or by another sensor.

The present invention may thus be summarized as an implantable antitachycardia therapy medical device. Such therapy device includes: (1) heart rate detection circuitry that detects a heart rate; (2) antitachycardia therapy circuitry that generates therapy signals for application to a heart when the heart rate detected by the heart rate detection circuitry exceeds a rate threshold signal; (3) a physiologic sensor that generates a sensor signal as a function of a sensed physiological parameter; and (4) sensor processing circuitry coupled to the physiologic sensor and the heart rate detection circuitry, with the sensor processing circuitry adjusting the rate threshold signal as a prescribed function of the sensor signal.

Advantageously, in a therapy device made in accordance with the present invention, the rate threshold signal is automatically adjusted as a function of the physiological parameter sensed by the physiologic sensor. The physiological parameter is selected as one that drives or predicts the natural heart rate, e.g., physical activity. Thus, the physiological parameter advantageously determines, at least in part, when the therapy signals are to be generated by the antitachycardia therapy circuitry. Because the physiological parameter drives the heart rate, the risk is minimized that a fast natural heartbeat caused by normal conditions, e.g., physical activity (exercise), might be interpreted by the antitachycardia therapy circuitry as an arrhythmia for which therapy signals are needed. On the other hand, because the physiological parameter is not driven by the heart rate, the threshold signal is not adjusted upon the onset of a valid arrhythmia, thereby allowing such a valid arrhythmia to be readily detected by the rate detection circuitry.

BRIEF DESCRIPTION OF THE DRAWINGS

The above and other aspects, features and advantages of the present invention will be more apparent from the Detailed Description of the Invention presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Implantable medical devices with which the present invention may be used include pacemakers and implantable cardioverter-defibrillators (ICDs). The details associated with the design and fabrication of such medical devices are known and practiced in the art, and hence, such details will not be presented herein. Representative pacemaker designs, for example, are shown in U.S. Pat. Nos. 4,712,555; 4,940,052; and 5,309,919; and U.S. patent application (assigned to the same assignee as is the present application) Ser. No. 07/846,460, filed Mar. 2, 1992, entitled "Method and System for Recording and Reporting a Sequential Series of Pacing Events." Typical pacemaker designs that include antitachycardia therapy features are shown in U.S. Pat. Nos. 4,788, 980 and 5,103,822. Similarly, representative ICD devices and designs are shown in U.S. Pat. Nos. 4,787,389; 4,989, 602; and 5,350,401; and U.S. patent application Ser. No. 07/979,083, filed Nov. 19, 1992, entitled "Electrically Programmable Polarity Connector for an Implantable Body Tissue Stimulator" (assigned to the same assignee as is the present application). All of the above patents and patent applications are incorporated herein by reference.

In general, an implantable medical device having arrhythmia detection and treatment features includes rate detection circuitry that monitors the occurrence of cardiac activity, e.g., heartbeats, as manifest by the electrogram (EGM) of the heart. The EGM, as is known in the art, includes P-waves, manifesting the depolarization (and presumably the subsequent contraction) of the atria of the patient's heart; and R-waves, manifesting the depolarization (and presumably the subsequent contraction) of the ventricles. Because the ventricles include muscle tissue that is much more massive than the atrial muscle tissue, the R-wave is a much larger signal than the P-wave, and is hence easier to detect. Thus, it is not uncommon for many implantable medical devices to only sense the R-wave, and to monitor the time interval between successive R-waves in order to ascertain the detected heart rate.

Naturally occurring P-waves and/or R-waves may be referred to as sinus P-waves or conducted R-waves, and the heart rate resulting from sinus P-waves and conducted R-waves may be referred to as the normal sinus rhythm (NSR) or natural sinus rate of the heart. The primary function of a pacemaker is to monitor the rate of the heart and to provide pacemaker-generated stimulation pulses to cause the atrium and/or ventricle to depolarize, and hence contract, in the event that the heart rate is too slow. The pacemaker thus paces the heart so that it maintains a rhythm, or heart rate, that is at least equal to a prescribed rate, refer red to as the "pacing rate." Many modern pacemakers include the capability of automatically adjusting the pacing rate in order to track the sensed physiological needs of the patient, e.g., increasing the pacing rate in the event that the physical activity of the patient increases. See e.g., U.S. Pat. Nos. 4,428,378; 4,576,183; or 4,940,052.

In contrast to pacemakers, the primary function of an ICD is to monitor the heart rate and provide appropriate stimulation pulses, or shock pulses, in the event that the heart rate becomes too fast (tachycardia), chaotic (fibrillation), or stops (asystole). All such conditions are referred to herein as cardiac "arrhythmias," and it is thus the primary function of an ICD to detect the occurrence of cardiac arrhythmias and to automatically apply a prescribed treatment aimed at stopping a perceived cardiac arrhythmia.

Many pacemakers include arrhythmia detection and treatment capabilities. See, e.g., U.S. Pat. Nos. 4,712,556; 4,788, 980; and 5,103,822, all of which are incorporated herein by reference. Also, many ICDs include pacing capabilities. The present invention has applicability to all such implantable medical devices, i.e., to devices that sense the occurrence of cardiac arrhythmias so that appropriate therapy can then be applied to stop or treat such arrhythmias.

Cardiac arrhythmias are typically detected by monitoring the heart rate, as evident, e.g., by the rate at which R-waves and/or P-waves occur in the EGM. If the heart rate exceeds a prescribed threshold reference value, referred to as a "detection rate threshold," then it is assumed that a tachyarrhythmia maybe present. If the detected heart rate is less than the prescribed threshold reference value, then it is assumed that there is no tachyarrhythmia. Sometimes, other parameters may also be monitored in addition to the heart rate, and an arrhythmia is assumed to exist only if the heart rate and the other conditions (or some combination thereof) are all present.

Figure 1:
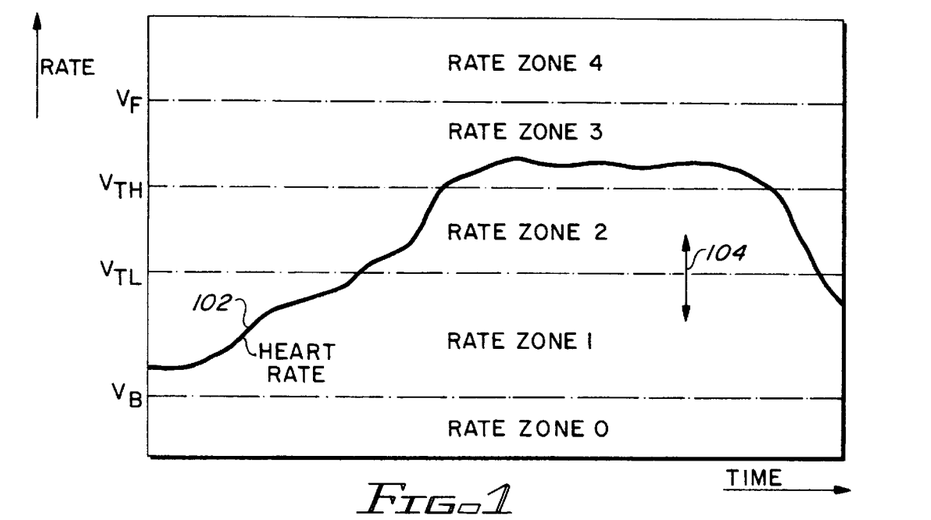
FIG. 1 shows a heart rate verses time graph that illustrates a typical variation of the heart rate of a patient's heart in normal sinus rhythm, and further depicts the various rate zones that may be used with an implantable antitachycardia device.

A graphical representation is shown in FIG. 1 that illustrates the manner in which arrhythmias are detected and classified in accordance with the present invention. FIG. 1 shows a typical heart rate of a patient in normal sinus rhythm, line 102, as a function of time. In FIG. 1, time is the horizontal axis, and the heart rate, usually expressed in beats per minute (bpm) is the vertical axis. The heart rate 102 starts at a relatively low rate (e.g., at an "at rest" rate, which for many patients may be on the order of 70 bpm) at the left of the graph, and then gradually increases as a function of time, as might occur, e.g., if the patient were to begin exercising. The heart rate 102 then levels off, near the center of the graph, an eventually begins its return back to the rest rate.

In order to classify the heart rate at any given time, the heart rate is compared to a plurality of rate threshold reference values, or "detection rate thresholds." A first rate threshold reference value is shown in FIG. 1 as the straight line labeled $V_B$. The reference rate $V_B$ is typically a very low rate, e.g., 50 bpm, and any heart rate that is less than $V_B$ thus represents a very slow heart rate, i.e., a bradycardia condition (one form of arrhythmia), for which some sort of treatment is needed. A second rate threshold reference value is shown in FIG. 1 as the straight line labeled $V_{TL}$. The reference rate $V_{TL}$ is typically a moderately fast rate, e.g., 135–170 bpm, and any heart rate that is greater than $V_{TL}$ represents a potential ventricular tachycardia condition (another form of arrhythmia) for which a first type of tachycardia therapy may be needed. Similarly, a third rate threshold reference value is shown in FIG. 1 as the straight line labeled $V_{TH}$. The reference rate $V_{TH}$ is typically a fast rate, e.g., 170–220 bpm, and any heart rate that is greater than $V_{TH}$ represents another type of potential ventricular tachycardia condition for which a second type of tachycardia therapy may be need. Still further, a fourth rate threshold reference value is shown in FIG. 1 as the straight line $V_F$. The reference rate $V_F$ is a very fast rate, e.g., greater than 220 bpm, and any heart rate that is greater than $V_F$ usually indicates a ventricular fibrillation condition (a serious, life threatening type of arrhythmia) for which appropriate therapy is needed immediately.

The various threshold reference values shown in FIG. 1 thus define various rate zones. That is, a first rate zone, Zone 0, comprises a zone that is bounded at its upper or maximum value by the reference rate $V_B$. Thus, any rate that is less than the reference rate $V_B$ falls within Zone 0 and signifies a possible bradycardia condition. (Hence, Zone 0 may be referred to as a bradycardia rate zone.)

Another rate zone, Zone 1, is bounded at the lower end by the reference rate $V_B$ and at the upper end by the reference rate $V_{TL}$. Any rate that falls within Zone 1 is probably a normal rate, and hence Zone 1 may be referred to as the normal rate zone.

Yet another zone, Zone 2, is bounded at the lower end by the reference rate $V_{TL}$, and at the upper end by the reference rate $V_{TH}$. Any heart rate that falls within Zone 2 could signify a tachycardia, and hence Zone 2 may be referred to as a first level tachycardia zone.

Still another zone, Zone 3, is bounded at the lower end by the reference rate $V_{TH}$, and at the upper end by the reference rate $V_F$. A heart rate that falls within Zone 3 more than likely evidences the existence of a tachycardia. Hence, Zone 3 may be considered as a second level tachycardia zone.

A final rate zone, Zone 4, is shown in FIG. 1 as being bounded at the lower end by the reference rate $V_F$, and being unbounded at the upper end. A heart rate that falls within Zone 4 signifies the presence of an extremely rapid heart rate, which probably evidences the existence of ventricular fibrillation. Thus, Zone 4 may be considered as a fibrillation zone.

It is to be understood that while four rate zones are illustrated in FIG. 1, such is only exemplary. Any number of rate zones may be used, e.g., two or more, depending upon the particular needs and function of the antitachycardia device that is employed. For example, in a simple antitachycardia detection and treatment device, only two rate zones will typically be used, separated by a single rate threshold reference value, $V_T$. Any heart rate less than the threshold reference $V_T$ is considered as falling within the normal rate zone, and any heart rate greater than the threshold reference $V_T$ is considered as falling within a tachycardia rate zone. If the heart rate falls within the tachycardia rate zone, then such rate may thus represent a condition for which antitachycardia therapy is required.

The use of a plurality of rate zones as shown in FIG. 1 advantageously permits a wide variety of different arrhythmia-terminating therapies to be used. Thus, the particular needs of the patient being treated, as well as the particular type of therapy that has been found to be most effective for a given type or arrhythmia, can be considered in tailoring an appropriate therapy for a given patient. For example, if the detected heart rate of the patient falls within the normal rate zone, Zone 1, then the medical device simply performs its normal function (which may be providing stimulation pulses on demand at the pacing rate, if the device is a pacemaker; or it may be alerted to detect tachyarrhythmias if the device is an ICD).

Should the detected heart rate enter the first level tachycardia zone, Zone 2, then an approriate antitachycardia therapy may be triggered. Such therapy may comprise providing a particular sequence of stimulation pulses, or scanning stimulation pulses in accordance with a prescribed pattern, or providing a low level shock pulse. There are numerous antitachycardia therapies known in the art, see, e.g., U.S. Pat. Nos. 3,942,534; 4,442,459; 4,554,920; 4,574, 437; 4,574,437; 4,712,556; 4,787,389; 4,788,980; 5,074, 308; 5,103,822; and 5,350,401, any of which, or equivalent or other therapies, could be invoked upon entering Zone 2.

In like manner, should the detected heart rate enter the second tachycardia zone, Zone 3, or the fibrillation zone, Zone 4, then appropriate therapies are also invoked in an attempt to terminate the arrhythmia condition manifest by such heart rate. For example, an appropriate therapy for a heart rate falling within Zone 3 may be a different sequence of stimulation pulses, a different or more rapid scanning pattern, double pulsing, a moderate level shock pulse, or the like. An appropriate therapy treatment for a heart rate falling within Zone 4 could be one or more high energy defibrillation pulses or shocks.

Thus, as described above, an implantable medical device that includes antitachycardia or other arrhythmia-treating features is able to sense the heart rate, classify the heart rate as falling within one or more rate zones, and then act upon the classified heart rate, alone or in combination with other approriate parameters, to automatically apply an appropriate arrhythmia-terminating therapy when needed.

The present invention provides for the automatic adjustment of one or more of the detection rate thresholds, i.e., the rate threshold reference signals, used by the implantable medical device. For example, with reference to FIG. 1, the present invention may automatically adjust the threshold reference $V_{TL}$ up or down, as suggested by the arrow 104, as a function of whether it is anticipated that the patient's heart rate will naturally increase or decrease. With such adjustment, the risk is minimized of triggering a Zone 2 therapy when such therapy is not needed.

To illustrate, assume that the threshold reference $V_{TL}$ is set at 130 bpm. If the patient is at rest, and his or her heart rate suddenly jumps to a value greater than 130 bpm, then a tachycardia condition is probably present, and antitachycardia therapy is appropriate. However, if the patient begins to exercise, e.g., starts to run, then it is quite likely that his or her natural heart rate may reach a value greater than 130 bpm. However, even though the heart rate exceeds the threshold reference $V_{TL}$, antitachycardia therapy would not be appropriate because an arrhythmia is not present. The present invention thus advantageously adjusts the threshold reference $V_{TL}$ so that it permits the anticipated natural heart rate to occur. In the illustration given, for example, the invention adjusts the threshold reference $V_{TL}$ up to a rate of, e.g., 160 or 170 bpm once it senses that the patient is exercising, but does not adjust $V_{TL}$ at all if the patient is at rest. Thus, the antitachycardia therapy is not invoked when the patient exercises and his or her heart rate exceeds 130 bpm, but would be invoked if his or her heart rate exceeds 130 bpm while it appears that the patient is at rest (not exercising).

The determination as to whether it is anticipated that the heart rate will increase or decrease is made by monitoring a physiologic parameter as sensed through an appropriate sensor. The physiologic parameter should be selected to be a parameter that correlates to the patient's natural sinus heart rate, not one that is driven by the heart rate. A preferred physiologic parameter suitable for this purpose is physical activity. Advantageously, physical activity can be easily sensed using, e.g., a piezoelectric sensor, see e.g., U.S. Pat. No. 4,940,053, or a motion sensor, such as is shown in U.S. Pat. No. 4,771,780 or 4,846,195, which patents are incorporated herein by reference. Other types of physiologic parameters that would be suitable for purposes of the present invention include blood flow, blood pressure, oxygen saturation, and partial pressure of oxygen.

The sensor, which is usually included within or coupled to the medical device, generates a raw sensor signal indicative of the physiologic parameter being monitored. The raw sensor signal, after suitable processing, may be used directly as the detection rate threshold signal (e.g., as the threshold reference $V_{TL}$) or as a control signal from which the detection rate threshold signal is obtained.

In some embodiments of the invention, only one of the threshold reference signals (e.g., $V_{TL}$) is automatically adjusted as a function of the sensed physiologic parameter, with the other threshold reference signals (e.g., $V_{TH}$, $V_F$, and $V_B$) being programmed to a fixed value which does not change until reprogrammed. In such instance, the adjustable threshold reference signal is defined by a prescribed transfer function that relates the value of the raw sensor signal to the threshold reference signal. Hence, when only one threshold reference signal is adjusted in this manner, the width of the rate zone (i.e., the separation between its lower and upper limits) varies, e.g., from being wide to thin, as a function of the sensed physiologic parameter.

In other embodiments of the invention, more than one of the threshold reference signals used to define the various rate zones (e.g., both $V_{TL}$ and $V_{TH}$) may be automatically adjusted as a function of the sensed physiologic parameter. In such case, each adjusted threshold reference signal may vary the same as the other reference signals, except for an offset, in which case an entire rate zone, e.g., Zone 2, may rove up or down as a function of the sensed physiologic parameter; or each adjusted threshold reference signal nay vary differently from the other reference signals, in which case the shape of the rate zone (as defined by its upper and lower boundaries) may change as a function of the sensed physiologic parameter.

In still other embodiments of the invention, separate sensors may be used for sensing different physiologic parameters, with each physiologic parameter being used to define a different threshold reference signal.

Further, where the implantable medical device comprises a rate-responsive pacemaker, which pacemaker includes its own sensor for sensing if the pacing rate of the pacemaker should change, the same sensor may advantageously be used by the rate-responsive pacemaker as is used by the present invention for the automatic adjustment of the detection rate threshold. However, it is important to recognize that when the same sensor is shared between a rate-responsive pacemaker and the detection rate threshold adjustment circuitry, the raw sensor signal is separately processed, or otherwise separately handled, so as to allow the raw sensor signal to be used for two separate functions: (1) rate-responsive pacing; and (2) automatic adjustment of the detection rate threshold.

Figure 2:
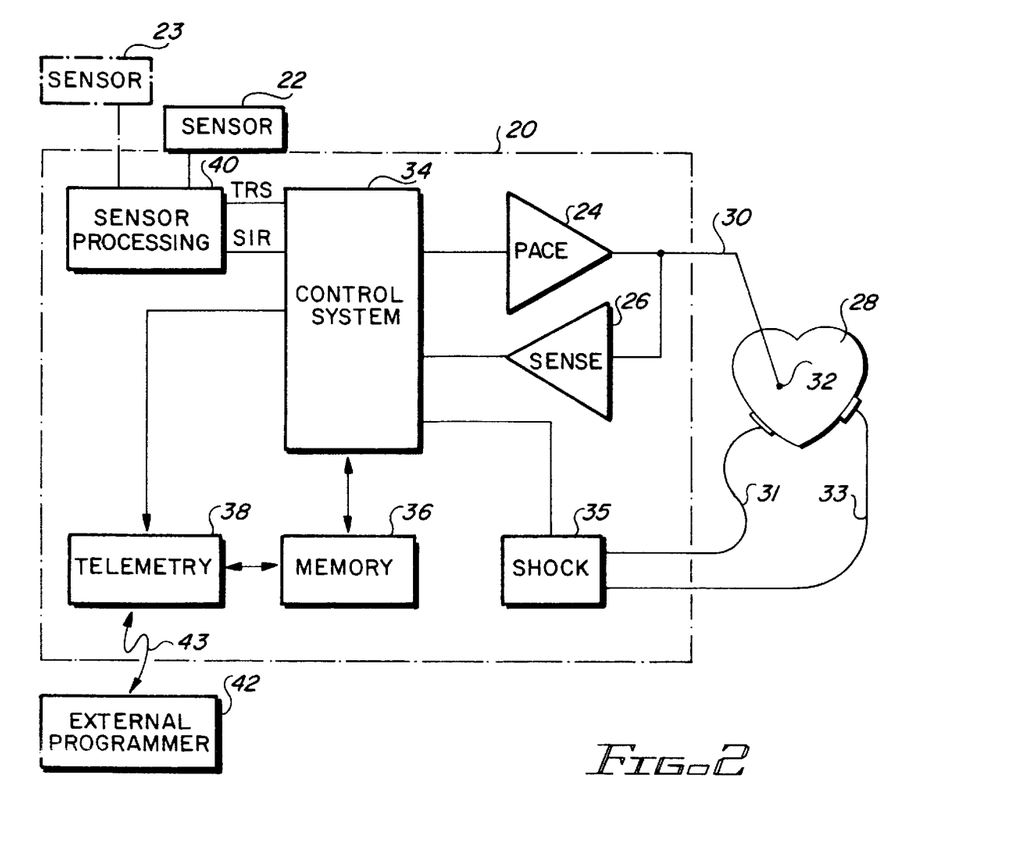
FIG. 2 is block diagram of an implantable device made in accordance with the present invention.

A simplified block diagram of the implantable medical device 20 of the present invention is illustrated in FIG. 2. The implantable device 20 is illustrated coupled to a heart 28 by way of an implantable stimulation lead 30. The lead 30 is shown as a unipolar lead, having a tip electrode 3. While a single-chamber unipolar system is shown, this is only to illustrate the basic functional blocks. It is understood that one skilled in the art could adapt the present invention to be used in either a dual-chamber device or with bipolar leads.

Controlling the device 20 is a control system 34. As is well known in the art, the control system 34 could be constructed from dedicated logic and timing circuitry, state machine circuitry, or a microprocessor.

The control system 34 is coupled to a pacing, or stimulation, channel 24 and a sensing channel 26. The pacing channel 24 includes a pulse generator circuitry for generating stimulation pulses of a prescribed pulse width amplitude and rate, as is commonly done in a pacemaker.

The sensing channel 26 includes amplifiers, filters, and signal conditioners, as needed, in order to properly sense the EGM signals from the heart (e.g., the R-waves and/or P-waves). The sensing channel may further be divided into an atrial channel (to sense P-waves) and a ventricular channel (to sense R-waves).

The control system 34 is also coupled to a shocking channel 35. The shocking channel 35 include defibrillation circuitry for storing and discharging low and high energy shocking pulses to the heart over the leads 31 and 33, as is commonly done in an implantable cardioverter-defibrillator (ICD) device. Although it appears from FIG. 2 that the pacing and sensing channels share the same implantable lead 30 and is separate from the shocking leads 31 and 33, it is also known in the art to combine a shocking electrode into the implantable lead 30 for either endocardial placement within the heart, or for epicardial placement on the out side of the heart.

Also connected to the control system 34 is a memory circuit 36, a telemetry circuit 38, and a sensor processing circuit 40. The memory circuit 34 has control variables and other signals stored therein that are used by the control system 34 as it controls the operation of the device 20. The memory circuit 34 may also have EGM data signals stored therein, or other event signals obtained through the sensing channel 26, or data signals obtained by monitoring the status of the device 20.

The telemetry circuit 38 provides a way of noninvasively interfacing with the memory circuit 36 and the control system 34 from an external (i.e., non-implanted) location using an appropriate external programmer 42. A telecommunicative link 43 is established between the programmer 42 and the telemetry circuit 38, as is known in the art. Through this link 43, telemetry circuit 38 and the external programmer 42, a physician or other medical personnel enters appropriate control signals so as to program the device 20 to operate in a prescribed manner. Further, through the link 43, the telemetry circuit 38, and the external programmer 42, EGM data signals and status signals stored in the memory 36, or generated within the control system 34, may be monitored by the physician or other medical personnel. The memory circuit 36, telemetry circuit 38, and external programmer 42 may be of conventional design.

The sensor processing circuit 40 interfaces with a sensor 22, and any other sensors 23, and receives and processes the raw sensor signal(s) therefrom. Such processing includes converting the raw sensor signal(s) to an appropriate threshold reference signal (TRS) that is delivered to the control system 34. The threshold reference signal is then used by the control system 34 to define the boundaries of the appropriate rate zone(s). Further, where the device 20 includes rate-responsive pacing features, and where the sensor 22 is shared so as to provide both rate-responsive and auto detection rate threshold adjustment, the sensor processing circuit 40 also provides a separate sensor indicated rate (SIR) signal. The SIR signal is then used to support the rate-responsive pacing features of the device 20.

While the sensor 22, and any other additional sensors 23, is shown as being outside of the device 20, it is to be understood that the sensors 22 and/or 23 may be included within, or attached to, the device 20.

Figure 3:
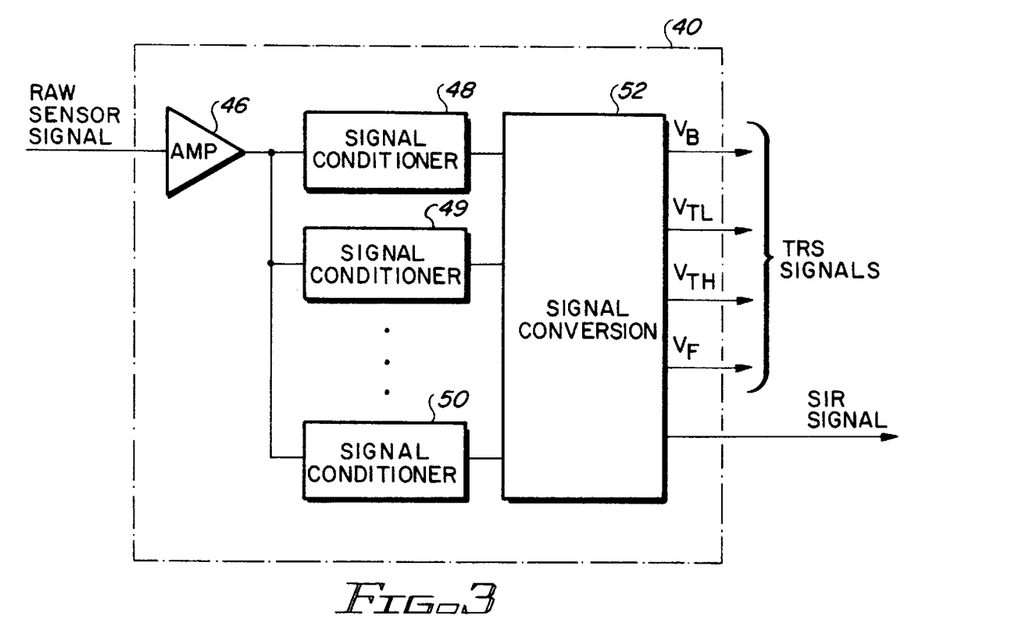
FIG. 3 is a functional block diagram of the sensor processing circuit of the device shown in FIG. 2.

In FIG. 3, a functional block diagram of the sensor processing circuit 40 is shown. The circuit 40 includes an amplifier 46 that receives the raw sensor signal from the sensor 22 (FIG. 1). If more than one sensor 22 is used, resulting in more than one raw sensor signal, then additional amplifiers are used for each raw sensor signal, as required. After amplification, the sensor signal is applied to signal conditioning circuits 48–50. Each signal conditioner 48–50 conditions or pre-processes the amplified raw signal in a prescribed manner. For example, the signal conditioner 48 may comprise a low pass filter that filters out the high frequency components of the amplified raw sensor signal. The signal conditioner 49 may comprise a band-bass filter that filters out all of the frequency components of the amplified raw sensor signal except those within a specified bandwidth. The signal conditioner 50 may comprise a rectifier and filter circuit that determines the energy content of the raw sensor signal (see, e.g., U.S. Pat. No. 4,940,053). As many signal conditioning circuits are used as are needed to properly condition the amplified raw sensor signal(s) for conversion to the threshold reference signals.

Typically, the signal conditioner circuits 48–50 will further normalize the magnitude of the signals that are conditioned thereby. Thus, for example, the conditioned signal form the conditioner 48 may be normalized to assume a value from 0 to 3 volts. Those of skill in the art will recognize that, in some instances, the function of amplification provided by the amplifier 46, and the functions of signal conditioning (e.g., signal filtering, and normalizing provided by the signal conditioning circuits 48–50) may be performed in a single amplifier/filter circuit.

After being conditioned by the signal conditioners 48–50, the conditioned signals are applied to a signal conversion circuit 52. The signal conversion circuit 52, which may include analog-to-digital (A/D) conversion, effectively uses a specified transfer function to transfer the conditioned sensor signals to an appropriate threshold reference signal (TRS). When an A/D converter is used as part of the conversion function, the output of the A/D converter may also be further normalized, e.g., to assume a value that varies from 0 to 32.

Figure 4:
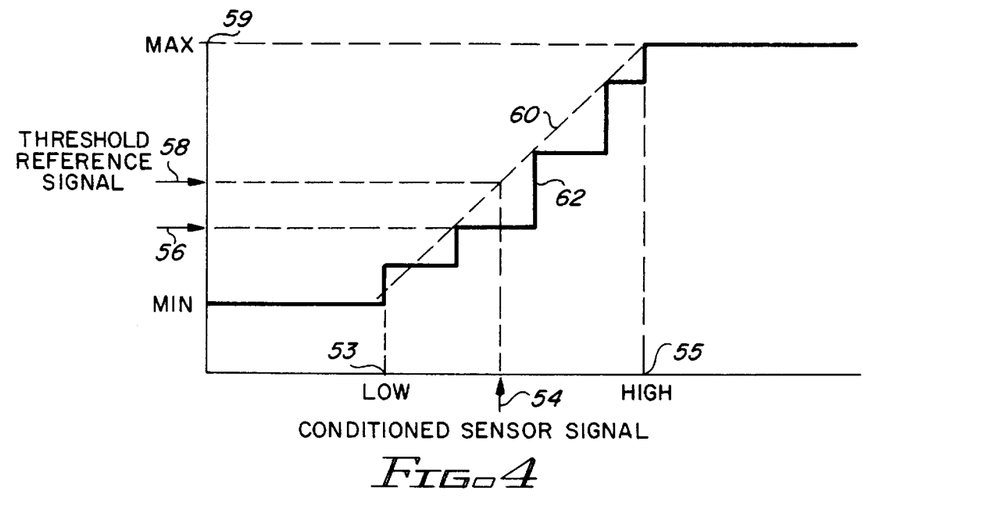
FIG. 4 illustrates a representative transfer function used by the sensor processing circuit of FIG. 3.

Two representative transfer functions used by the signal conversion circuit 52 are graphically shown in FIG. 4. As seen in FIG. 4, the conditioned sensor signal (the "input signal" to the signal conversion circuit 52) is represented along the horizontal axis of the transfer function representation, and the threshold reference signal(s) (the "output signal" of the signal conversion circuit 52) is represented along the vertical axis of the transfer function representation.

A first transfer function shown in FIG. 4 is a linear transfer function between minimum and maximum points, and is represented by the dashed line 60. When such linear transfer function 60 is used, the threshold reference signal comprises a MIN value 57 whenever the input signal is less than a LOW value 53; a MAX value 59 whenever the input signal is greater than a HIGH value 55; and a value intermediate the MIN and MAX values whenever the input signal is somewhere between the LOW value 53 and the HIGH value 55. The linear relationship is represented by the line 60 for input signal values between the LOW and HIGH values. For example, if the input signal has a value represented by the point 54, then the threshold reference signal is determined by traversing a vertical line from the point 54 to the line 60, and then a horizontal line to the threshold reference signal (TRS) axis, which is a value represented by the point 58.

A linear transfer function, such as is represented in FIG. 4 by the line 60, for the threshold reference signal (TRS) may also be expressed mathematically as:

$$\begin{aligned} TRS &= \text{MIN, for } V_{IN} < V_{LOW}, \\ &= a + kV_{IN}, \text{ for } V_{LOW} < V_{IN} < V_{HIGH}, \\ &= \text{MAX, for } V_{IN} > V_{HIGH}, \end{aligned}$$

where a is an offset value, k is a scale factor, $V_{LOW}$ corresponds to the LOW value 53, $V_{HIGH}$ corresponds to the HIGH value 55, and $V_{IN}$ is the input signal to the signal conversion circuit 52.

Also shown in FIG. 4 is a second transfer function, or "stair-step" function, represented by the stair-step line 62. In accordance with such stair-step function, the threshold reference signal assumes a value that is defined by the relationship of the input signal to the stair-step line 62. For example, if the input signal is a value represented by the point 54, then the threshold reference signal is determined by drawing a vertical line up from the point 54 to the stair-step line 62, and then a horizontal line over from the stair-step line 62 to the threshold reference signal axis, to the point 56. Thus, as the input signal value changes, the threshold reference signal value also changes, in discrete steps, as defined by the stair-step line 62. Note that the stair-step line 62 is also bounded by upper and lower limits, which (for the function shown in FIG. 4) are the same as used for the linear relationship represented by the line 60.

As required, a separate transfer function is used for each of the threshold reference signals that are used by the device 20. For example, a first threshold reference signal function may be used to define $V_B$ as a function of the signal $V_{IN}$ obtained from the signal conditioner circuit 48. Similarly, a second threshold reference signal function may be used to define $V_{TL}$ as a function of the signal $V_{IN}$ obtained from the signal conditioner 49; and a third threshold reference signal function may be used to define $V_{TH}$ as a function of the signal obtained from the signal conditioner 50.

In some instances, the same transfer function may be used to define related threshold reference signals, e.g., the lower and upper limits of a given rate zone. In such instance, one of the threshold reference signals is defined by the specified function, and the other threshold reference signals are then defined in terms of the first threshold reference signal, e.g., to be a value determined by the first threshold reference signal plus an offset value.

As an example of representative values that may be used relative to defining the threshold reference signal, $V_{TL}$, assume that the input signal to the signal conversion circuit 52 is digitized and normalized to assume a value of between 0 and 32. Then, representative values for the LOW point 53 may be between 3 and 5, and for the HIGH point 55 between 27 and 29. Representative limits for the MIN and MAX values of $V_{TL}$ may be 120 and 170 bpm, respectively. Advantageously, such LOW and HIGH points of the input signal, or MIN and MAX value of the output signal are programmable, as needed, in conventional manner so that the transfer function can be customized to best meet the needs of a particular patient.

The amplifier 46, signal conditioner circuits 48–50, and signal conversion circuit 52 of the sensor processing circuit 40 shown in FIG. 3 may be realized using analog or digital circuits, e.g., integrated circuits, commercially available from numerous vendors. Alternatively, much of the signal conditioning and signal conversion function may be carried out using a microprocessor that is appropriately programed to carry out the above-described functions. In such instance, after appropriate amplification and filtering of the raw sensor signal, the amplified and conditioned signal is converted to a digital signal, and made avail able to the microprocessor as a data input signal. The data input signal is then processed, e.g., normalized and converted to an appropriate threshold reference signal, as described above.

As further seen in FIG. 3, the signal conversion circuit 52 may also include the appropriate circuitry for generating the sensor indicated rate (SIR) signal used by the rate-responsive circuits of a rate-responsive pacemaker, in the event that rate-responsive pacing is one of the functions provided by the implantable medical device 20. Such SIR-generating circuitry may be of conventional design, e.g., as shown in U.S. Pat. No. 4,940,052, or may be as shown in U.S. patent application Ser. No. 07/844,818, filed Mar. 2, 1992, entitled "Method and System for Automatically Adjusting the Sensor Parameters of a Rate-Responsive Pacemaker", assigned to the same assignee as the present application, both of which are incorporated herein by reference.

Figure 5:
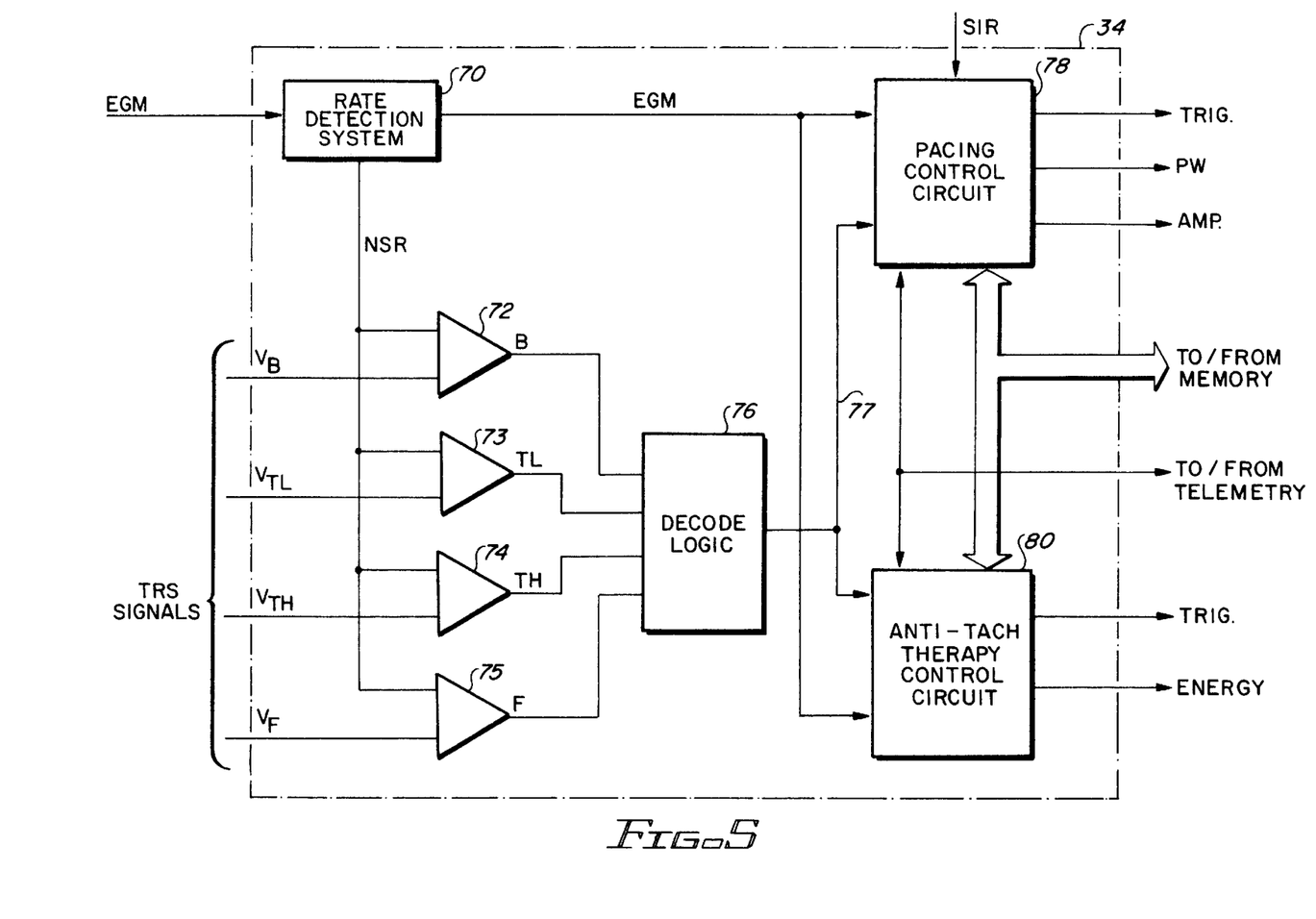
FIG. 5 is a functional block diagram of the control circuit of the device of FIG. 2.

In FIG. 5, there is illustrated a functional block diagram of the control system 34 of the medical device 20. As seen in FIG. 5, the system 34 includes rate detection circuitry 70, threshold detector circuits 72–75, decode logic 76, and pacing control circuitry 78 and antitachycardia therapy control circuitry 80. The rate detection circuitry 70 receives the EGM signal (R-waves and/or P-waves) from the sensing channel 26 (FIG. 2) and determines a natural heart rate therefrom. The EGM signals are also passed on to the pacing control circuitry 78, as well as the antitachycardia therapy control circuitry 80.

The heart rate signal is compared to the threshold reference signals using the threshold detection circuits 72–75. That is, the signal is heart rate compared to the threshold reference signal, $V_B$ using threshold circuit 72. If the heart rate is greater than $V_B$, then an output signal B of the threshold detector 72 assumes a high value, and if not, the output signal B assumes a low value. In a similar manner, the heart rate signal is compared to each of the threshold reference signals, $V_{TL}$, $V_{TH}$, and $V_F$, using threshold circuits 73, 74 and 75, respectively, to generate the output signals TL, TH, and F, respectively. Such output signals, B, TL, TH, and F are then applied to the decode logic 76. It is the function of the decode logic 76 to determine the particular rate zone wherein the heart rate signal falls. For example, if all of the threshold output signals B, TL, TH, and F are low, then that indicates the heart rate signal is presently in rate Zone 1 (FIG. 1). If all the threshold output signals are low but the TL signal, then that indicates the heart rate signal is in rate Zone 2. In a similar manner, a determination is made if the heart rate signal falls in any of the other rate zones. Thus, in this manner, an appropriate mode control signal is generated by the decode logic 76 and made available on signal line 77 that indicates the particular rate zone wherein the heart rate signal lies.

As is common in the art, the operation of the threshold circuits 72–75 may be performed on a sampled basis. In such case, the operation of a give threshold circuit 72–75 is sampled on a periodic basis, e.g., once each cardiac cycle, and the respective output signal, B, TL, TH or F is latched to a low or high value until the next sample time. Alternatively or conjunctively, the raw sensor signal applied to the sensor processing circuit 40 may also be sampled, in which case the threshold reference signal's are latched to a given value based on the latest sample taken.

The mode control signal available on signal line 77 is made available to both the pacing control circuitry 78 and the antitachycardia therapy control circuitry 80. Depending upon the rate zone indicated by the mode control signal, an appropriate therapy, or other operation (e.g., normal pacing), is then invoked by one of the pacing control or antitachycardia therapy control circuits. The pacing control circuit 78, for example, when invoked by the mode control signal, and when a normal heartbeat is not detected within the prescribed time interval, provides a trigger signal and pulse width and amplitude signals to the pacing channel so that a stimulation pulse of the specified pulse width and amplitude can be generated in the pacing channel. The antitachycardia therapy control circuit 80, when invoked by the mode control signal, provides appropriate trigger and energy signals to the pacing channel 24 (which may include a defibrillation output channel) so that a specified type of antitachycardia therapy is applied to the heart.

The pacing control circuit 78 may be the same as used in conventional implantable pacemakers, as described, e.g., in U.S. Pat. Nos. 4,712,555 or 4,940,052. Similarly, the antitachycardia therapy control circuit 80 may be the same as used in conventional ICD devices, as described, e.g., in U.S. Pat. Nos. 3,942,534; 4,574,437; or 4,989,602. The above '534 and '437 patents are incorporated herein by reference. For purposes of the present invention, the details associated with such pacing control circuit 78 or antitachycardia therapy control circuit 80 are not important. All that is required is that some sort of control circuit be used that provides the function of pacing or antitachycardia therapy in a prescribed manner.

Figure 6:
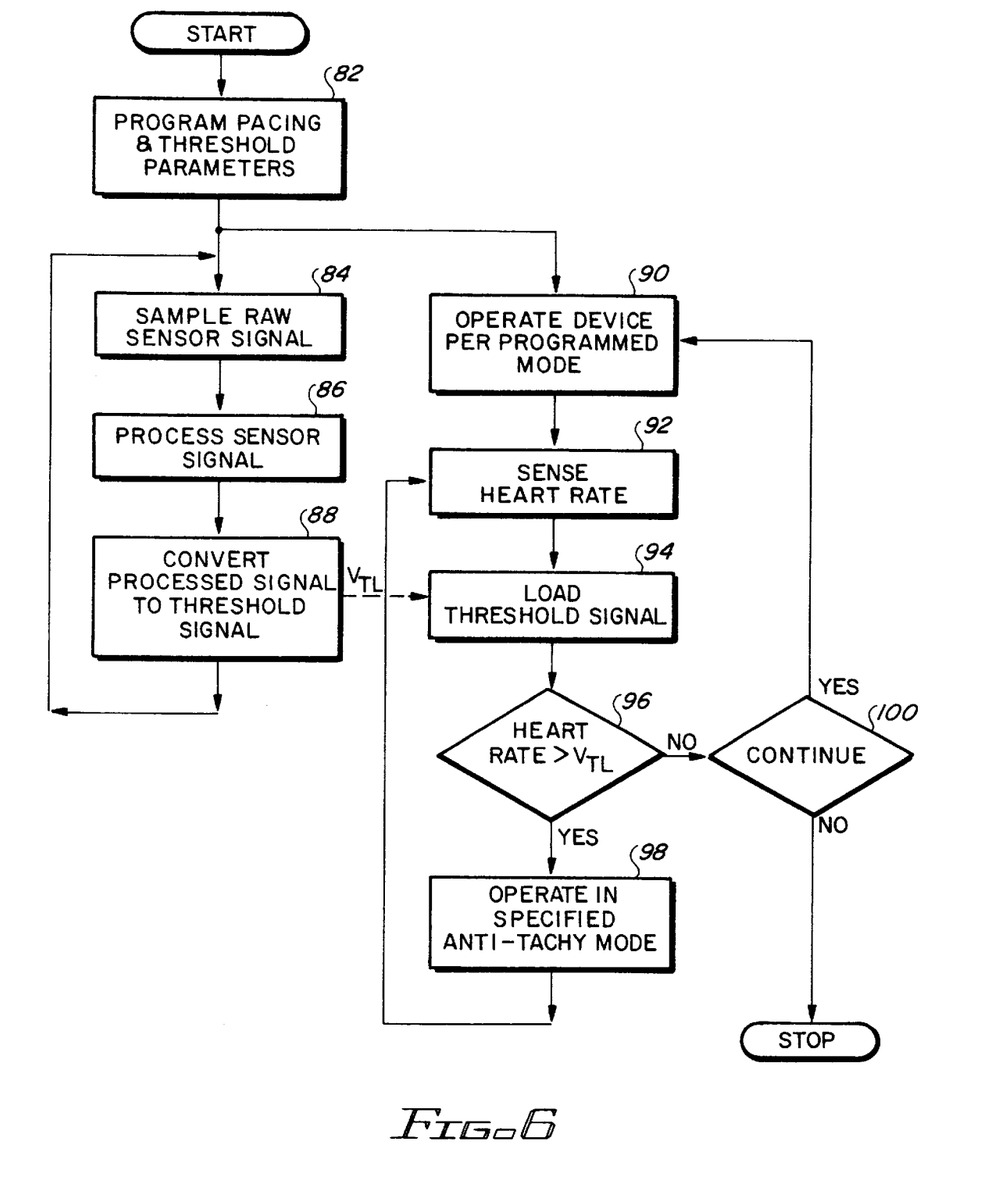
FIG. 6 is a flowchart that illustrates the automatic adjustment of the lower limit threshold signal in accordance with the present invention.

In FIG. 6, a flowchart is shown that illustrates the automatic adjustment of the threshold reference signal (TRS) value, $V_{TL}$, in accordance with the present invention. It is understood that a similar adjustment of the other threshold reference signal value $V_B$, $V_{TH}$, and $V_F$, if used, may also occur. In such flowchart, each main step is represented as a "box" or "clock" (with each block or box having a reference numeral) that is linked to the other steps by one-directional lines, thereby graphically illustrating the "flow" that occurs from one step to the next.

As seen in FIG. 6, a first step after enabling the automatic adjustment process is to program the pacing and threshold parameters that are used by the invention and by the other circuits of the implantable medical device (block 82). Such parameters include, e.g., the transfer function parameters that define the threshold reference signal, $V_{TL}$, as a function of the conditioned sensor signal, and the parameters that define the type of pacing or antitachycardia therapy that is to be invoked for each rate zone.

Once the pacing and threshold parameters have been programmed, two parallel processing paths are started. A first process path, represented by blocks 84, 86 and 88, relates to the processing of the sensor signal. Such processing includes sampling the raw sensor signal (block 84), processing the sensor signal (block 86), and converting the processed signal to the appropriate threshold reference signal (block 88). All of these sensor signal processing steps are carried out as described above in connection with FIGS. 3 and 4, or equivalent processing steps.

A second process path, represented by blocks 90–100, relates to the operation of the medical device. Such processing includes operating the device in accordance with its programmed mode (block 90). If the device is a pacemaker, for example, its programmed mode may be the DDD mode, or the DDI mode. At some point during a cardiac cycle while the device is operating according to its programmed mode, the intrinsic heart rate is sensed (block 92). Also, at an appropriate time, the threshold rate signal, $V_{TL}$, obtained from the processed sensor signal (block 88), is retrieved or otherwise made available for examination (block 94). If the heart rate is greater than the threshold rate signal, $V_{TL}$, (block 96), then that suggests an arrhythmia (e.g., a tachycardia) may be present, so the appropriate antitachycardia therapy may be invoked (block 98). After invoking such therapy for a prescribed time, the heart rate is again sensed (block 92), the latest value of the threshold reference signal is retrieve (block 94), and the comparison between the heart rate and the threshold reference signal is again made (block 96). This process continues until the arrhythmia (evidenced by the heart rate being greater than the threshold reference signal) is terminated. If the heart rate is less than the threshold reference signal, $V_{TL}$ (block 96), and if the operation of the device is to continue (block 100), then the operation of the device continues pursuant to its programmed mode (block 90), and the process repeats.

In the manner shown in FIG. 6, then, the implantable medical device automatically adjusts its threshold reference signal(s) as a function of the sensor signal(s) that is sensed and processed, and uses such threshold reference signal(s) to determine if an arrhythmia is present for which arrhythmia-terminating therapy is needed. For example, if the sensor signal indicates a high level of physical activity, then the threshold reference signal is accordingly automatically increased by an appropriate amount, thereby assuring that a high or fast natural sinus rate of the heart is not misinterpreted as an arrhythmia for which antitachycardia therapy might otherwise be invoked.

Thus, it is seen that the present invention provides an implantable antitachycardia medical device, i.e., an implantable pacemaker or an implantable cardioverter-defibrillator (ICD), wherein rate detection circuitry is utilized that minimizes the risk of incorrectly identifying and classifying a fast sinus rate as an arrhythmia for which antitachycardia therapy is needed.

It is further seen that the invention provides an implantable antitachycardia device that automatically adjusts its detection rate zone(s), e.g., by automatically adjusting the lower and/or upper limits of such rate zone(s), as a function of a sensed physiologic parameter of the patient, which physiologic parameter provides an indication as to whether the sinus heart rate is expected to change.

It is also seen that the invention provides an implantable rate-responsive antitachycardia pacemaker wherein a raw signal from a physiologic sensor used with the pacemaker independently provides: (1) the basis for deriving a sensor indicated rate (SIR) signal that sets the pacing rate of the pacemaker, and (2) the basis for adjusting the lower and/or upper limits of a detection rate zone(s) used by the pacemaker to detect when an arrhythmia (for which antitachycardia therapy is needed) is present.

While the invention herein disclosed has been described by means of specific embodiments and applications thereof, numerous modifications and variations could be made thereto by those skilled in the art without departing from the scope of the invention set forth in the claims.

What is claimed is:

1. An implantable antitachycardia stimulation device comprising:

pulse generating means for generating stimulation pulses to a patient's heart;

sensing means for sensing cardiac activity of the patient's heart;

first physiologic sensing means for sensing a physiologic parameter indicative of a normal heart rate, and for generating a first sensor signal representative of the sensed physiologic parameter;

control means, coupled to the pulse generating means, the sensing means, and the first physiological sensing means, for providing a prescribed antitachycardia therapy through the pulse generating means and for terminating a sensed cardiac arrhythmia, the control means including:

rate detection means for detecting the heart rate of the patient based on the cardiac activity sensed through the sensing means;

threshold means for generating at least two rate zone thresholds, a low rate zone threshold signal and a high rate zone threshold signal, the low rate zone threshold signal being a function of the first sensor signal, and the high rate zone threshold signal being a prescribed amount greater than the low rate zone threshold signal at least one rate zone threshold signal as a function of the first sensor signal; and comparator means for comparing the detected heart rate with the at least one rate zone threshold signal, for determining when the heart rate exceeds the at least one rate zone threshold signal, and for indicating that a cardiac arrhythmia is present.

2. The implantable stimulation device, as set forth in claim 1, wherein the first physiologic sensing means comprises a sensor that senses physical activity of the patient.

3. The implantable stimulation device, as set forth in claim 1, wherein the implantable stimulation device comprises:

second physiologic sensing means for sensing a second physiologic parameter of the heart, and for generating a second sensor signal representative of the second physiologic parameter;

rate-responsive pacing means for determining a sensor indicated rate (SIR) signal based on the second sensor signal, and for controlling the rate of stimulation pulses provided by the pulse generating means according to the sensor indicated rate.

4. The implantable stimulation device, as set forth in claim 3, wherein the second physiological sensing means is adapted to sense a physiologic parameter that is separate from the physiologic parameter sensed by the first physiological sensing means.

5. The implantable stimulation device, as set forth in claim 3, wherein:

the first physiologic sensing means and the second physiologic sensing means comprise a single sensor, and wherein the single sensor generates a raw sensor signal indicative of the sensed physiologic parameter; and the implantable stimulation device includes sensor processing means for generating the first sensor signal as a first function of the sensed physiologic parameter, and for generating the SIR signal as a second function of the sensed physiologic parameter.

6. An implantable antitachycardia stimulation device comprising:

pulse generating means for generating stimulation pulses to a patient's heart;

sensing means for sensing cardiac activity of the patient's heart;

first physiologic sensing means for sensing a physiologic parameter indicative of a normal heart rate, and for generating a first sensor signal representative of the sensed physiologic parameter;

control means, coupled to the pulse generating means, the sensing means, and the first physiological sensing means, for providing a prescribed antitachycardia therapy through the pulse generating means and for terminating a sensed cardiac arrhythmia, the control means including:

rate detection means for detecting the heart rate of the patient based on the cardiac activity sensed through the sensing means;

threshold means for generating at least two rate zone thresholds, a low rate zone threshold signal and a high rate zone threshold signal, the low rate zone threshold signal being a first function of the first sensor signal, and the high rate zone threshold signal being a second function of the first sensor signal; and comparator means for comparing the detected heart rate with the at least one rate zone threshold signal, for determining when the heart rate exceeds the at least one rate zone threshold signal, and for indicating that a cardiac arrhythmia is present.

7. The implantable stimulation device, as set forth in claim 6, wherein the first physiologic sensing means comprises a sensor that senses physical activity of the patient.

8. The implantable stimulation device, as set forth in claim 6, wherein the implantable stimulation device comprises:

second physiologic sensing means for sensing a second physiologic parameter of the heart, and for generating a second sensor signal representative of the second physiologic parameter;

rate-responsive pacing means for determining a sensor indicated rate (SIR) signal based on the second sensor signal, and for controlling the rate of stimulation pulses provided by the pulse generating means according to the sensor indicated rate.

9. The implantable stimulation device, as set forth in claim 8, wherein the second physiological sensing means is adapted to sense a physiologic parameter that is separate from the physiologic parameter sensed by the first physiological sensing means.

10. The implantable stimulation device as set forth in claim 8, wherein:

the first physiologic sensing means and the second physiologic sensing means comprise a single sensor, and wherein the single sensor generates a raw sensor signal indicative of the sensed physiologic parameter; and the implantable stimulation device includes sensor processing means for generating the first sensor signal as a first function of the sensed physiologic parameter, and for generating the SIR signal as a second function of the sensed physiologic parameter.

11. An implantable antitachycardia stimulation device comprising:

pulse generating means for generating stimulation pulses to a patient's heart;

sensing means for sensing cardiac activity of the patient's heart;

first physiologic sensing means for sensing a physiologic parameter indicative of a normal heart rate, and for generating a first sensor signal representative of the sensed physiologic parameter;

second physiologic sensing means for sensing a second physiologic parameter of the heart, and for generating a second sensor signal representative of the second physiolgic parameter;

rate-responsive pacing means for determining a sensor indicated rate (SIR) signal based on the second sensor signal, and for controlling the rate of stimulation pulses provided by the pulse generating means according to the sensor indicated rate;

control means, coupled to the pulse generating means, the sensing means, and the first physiological sensing means, for providing a prescribed antitachycardia therapy through the pulse generating means and for terminating a sensed cardiac arrhythmia, the control means including:

rate detection means for detecting the heart rate of the patient based on the cardiac activity sensed through the sensing means;

threshold means for generating at least one rate zone threshold signal as a function of the first sensor signal; and comparator means for comparing the detected heart rate with the at least one rate zone threshold signal, for determining when the heart rate exceeds the at least one rate zone threshold signal, and for indicating that a cardiac arrhythmia is present.

12. The implantable stimulation device, as set forth in claim 11, wherein the first physiologic sensing means comprises a sensor that senses physical activity of the patient.

13. The implantable stimulation device, as set forth in claim 11, wherein the implantable stimulation device comprises:

second physiologic sensing means for sending a second physiologic parameter of the heart, and for generating a second sensor signal representative of the second physiolgic parameter;

rate-responsive pacing means for determining a sensor indicated rate (SIR) signal based on the second sensor signal, and for controlling the rate of stimulation pulses provided by the pulse generating means according to the sensor indicated rate.

14. The implantable stimulation device, as set forth in claim 11, wherein the second physiological sensing means is adapted to sense a physiologic parameter that is separate from the physiologic parameter sensed by the first physiological sensing means.

15. An implantable antitachycardia therapy device, comprising:

heart rate detection means for detecting a heart rate;

antitachycardia therapy means for generating stimulation pulses for application to a heart when the detected heart rate exceeds a first threshold signal;

physiologic sensing means for generating a sensor signal as a function of a sensed physiologic parameter of the heart; and processing means, coupled to the physiologic sensing means and the heart rate detection means, for generating the first threshold signal such that the first threshold signal assumes a minimum value if the sensor signal is less than a low sensor signal value, and the first threshold signal assumes a maximum value if the sensor signal is greater than a high sensor signal value and wherein the relationship between the sensor signal and the first threshold signal intermediate the low sensor signal value and the high sensor signal value is linear.

16. The implantable antitachycardia therapy device, as set forth in claim 15, wherein the antitachycardia therapy means comprises:

means for generating a first type of therapy when the detected heart rate exceeds the first threshold signal, and for generating a second type of therapy when the detected heart rate exceeds a second threshold signal, the second threshold signal being greater than the first threshold signal, the second threshold signal being generated by the processing means.

17. The implantable antitachycardia therapy device, as set forth in claim 15, wherein the antitachycardia therapy means comprises:

threshold detection means for determining if the heart rate exceeds the first threshold signal, and if so generating a mode control signal; and therapy control means for generating a prescribed sequence of stimulation pulses in response to the mode control signal.

18. The implantable antitachycardia therapy device, as set forth in claim 17, wherein the threshold detection means includes means for detecting in which of a plurality of rate zones the heart rate lies.

19. The implantable antitachycardia therapy device, as set forth in claim 15 wherein the sensed physiologic parameter comprises physical activity.

20. An implantable antitachycardia therapy device, comprising:

heart rate detection means for detecting a heart rate;

antitachycardia therapy means for generating stimulation pulses for application to a heart when the detected heart rate exceeds a first threshold signal;

physiologic sensing means for generating sensor signal as a function of a sensed physiologic parameter of the heart; and processing means, coupled to the physiologic sensing means and the heart rate detection means, for generating the first threshold signal as a prescribed function of the sensor signal, wherein the prescribed function is defined such that the first threshold signal assumes a minimum value if the sensor signal is less than a low sensor signal value and assumes a maximum value if the sensor signal is greater than a high sensor signal value and assumes one of a plurality of threshold values intermediate the minimum value and the maximum value depending upon which of a respective plurality of sensor signal reference values intermediate the low and high sensor signal values is exceeded by the sensor signal.

21. The implantable antitachycardia therapy device, as set forth in claim 20, wherein the antitachycardia therapy means comprises:

means for generating a first type of therapy when the detected heart rate exceeds the first threshold signal, and for generating a second type of therapy when the detected heart rate exceeds a second threshold signal, the second threshold signal being greater than the first threshold signal, the second threshold signal being generated by the processing means.

22. The implantable antitachycardia therapy device, as set forth in claim 20, wherein the antitachycardia therapy means comprises:

threshold detection means for determining if the heart rate exceeds the first threshold signal, and if so generating a mode control signal; and therapy control means for generating a prescribed sequence of stimulation pulses in response to the mode control signal.

23. The implantable antitachycardia therapy device, as set forth in claim 22, wherein the threshold detection means includes means for detecting in which of a plurality of rate zones the heart rate lies.

24. The implantable antitachycardia therapy device, as set forth in claim 20, wherein the sensed physiologic parameter comprises physical activity.

25. A method for adjusting the detection rate threshold in an implantable antitachycardia therapy device, the device including rate detection means for detecting a heart rate, sensor means for sensing a physiologic parameter, and antitachycardia therapy means for selectively generating a prescribed stimulation sequence for terminating a sensed tachycardia, the method comprising the steps of:

(a) detecting the heart rate with the rate detection means;

(b) sensing the physiologic parameter with the sensor means;

(c) automatically defining a detection rate threshold signal by defining a minimum detection rate threshold signal corresponding to physiologic parameters less than a low physiologic parameter, defining a maximum detecting rate threshold signal corresponding to physiologic parameters greater than a high physiologic parameter and defining the detection rate threshold signal to assume a linear relationship relative to the sensed physiologic parameter for physiologic parameters intermediate the low and high physiologic parameters;

(d) determining if the sensed heart rate is greater than the detection rate threshold signal;

(e) invoking a programmed mode of operation of the therapy device in the event that the sensed heart rate is less than the detection rate threshold signal; and (f) invoking an antitachycardia therapy node of operation of the therapy device in the event that the sensed heart rate is greater than the detection rate threshold signal; whereby the detection rate threshold signal is automatically adjusted as a function of the sensed physiologic parameter, and further whereby the antitachycardia therapy mode is invoked only when the detected heart rate exceeds the adjusted detection rate threshold signal.

26. The method, as set forth in claim 25, wherein:
step (c) comprises automatically defining a plurality of detection rate threshold signals;
step (d) comprises determining if the sensed heart rate exceeds one of the detection rate threshold signal; and
step (f) comprises invoking an appropriate one of a plurality of antitachycardia therapy modes of operation whenever the heart rate exceeds one of the detection rate threshold signals.

27. An implantable antitachycardia therapy device, comprising:
heart rate detection means for detecting a heart rate;
antitachycardia therapy means for generating stimulation pulses for application to a heart when the detected heart rate exceeds a first threshold signal;
physiologic sensing means for generating a sensor signal as a function of a sensed physiologic parameter of the heart; and
processing means, coupled to the physiologic sensing means and the heart rate detection means, for generating at least a low rate zone threshold signal and a high rate zone threshold signal, the low rate zone threshold signal being a first function of the sensor signal, and the high rate zone thresold signal being a second function of the sensor signal.

28. The implantable antitachycardia therapy device, as set forth in claim 27, wherein the antitachycardia therapy means comprises:
means for generating a first type of therapy when the detected heart rate exceeds the low rate zone threshold signal and for generating a second type of therapy when the detected heart rate exceeds the high rate zone threshold signal.

29. The implantable antitachycardia therapy device, as set forth in claim 27, wherein:
the processing means includes means for defining the first function such that the low rate zone threshold signal assumes a minimum value if the sensor signal is less than a low sensor signal value, and the low rate zone threshold signal assumes a maximum value if the sensor signal is greater than a high sensor signal value.

30. The implantable antitachycardia therapy device, as set forth in claim 29, wherein the processing means comprises:
means for defining the first function a being a linear relationship between the sensor signal and the low rate zone threshold signal intermediate the low sensor signal value and the high sensor signal value.

31. The implantable antitachycardia therapy device, as set forth in claim 29, wherein the processing means comprises:
means for defining the first function such that the low rate zone threshold signal assumes one of a plurality of threshold values intermediate the minimum value and the maximum value depending upon which of a respective plurality of sensor signal reference values intermediate the low and high sensor signal values is-exceeded by the sensor signal.

32. The implantable antitachycardia therapy device, as set forth in claim 27, wherein the antitachycardia therapy means comprises:
threshold detection means for determining if the heart rate exceeds the low rate zone threshold signal, and if so generating a mode control signal; and
therapy control means for generating a prescribed sequence of stimulation pulses in response to the mode control signal.

33. The implantable antitachycardia therapy device, as set forth in claim 32, wherein the threshold detection means includes means for detecting in which of a plurality of rate zones the heart rate lies.

34. The implantable antitachycardia therapy device, as set forth in claim 27, wherein the sensed physiologic parameter comprises physical activity.

35. A method for adjusting the detection rate threshold in an implantable antitachycardia therapy device, the device including rate detection means for detecting a heart rate, sensor means for sensing a physiologic parameter, and antitachycardia therapy means for selectively generating a prescribed stimulation sequence for terminating a sensed tachyeardia, the method comprising the steps of:
(a) detecting the heart rate with the rate detection means;
(b) sensing the physiologic parameter with the sensor means;
(c) automatically defining at least two rate zone detection thresholds, a low rate zone detection threshold signal defined as a first function of the physiologic parameter sensed by the sensor means and a high rate zone detection threshold signal defined as a second function of the physiologic parameter sensed by the sensor means;
(d) determining if the sensed heart rat is greater than the low rate zone detection threshold signal;
(e) invoking a programmed mode of operation of the therapy device in the event that the sensed heart rate is less than the low rate zone detection threshold signal; and
(f) invoking an antitachycardia therapy mode of operation of the therapy device in the event that the sensed heart rate is greater than the detection rate threshold signal; and
whereby the low rate zone detection threshold signal is automatically adjusted as a function of the sensed physiologic parameter, and further whereby the antitachycardia therapy mode is invoked only when the detected heart rate exceeds the adjusted low rate zone detection threshold signal.

36. The method, as set forth in claim 35, wherein:
step (c) comprises automatically defining a plurality of rate zone detection threshold signals;
step (d) comprises determining if the sensed heart rate exceeds one of the rate zone detection threshold signals; and
step (f) comprises invoking an appropriate one of a plurality of antitachycardia therapy modes of operation whenever the heart rate exceeds one of the rate zone detection threshold signals.

37. The method, as set forth in claim 35, wherein step (c) comprises:
   defining the low rate zone detection threshold signal as corresponding to physiologic parameters less the a low physiologic parameter;
   defining the high rate-zone detection threshold signal as corresponding to physiologic parameters greater than a high physiologic parameter; and
   defining the rate zone detection threshold signal to be a prescribed function of the physiologic parameter for physiologic parameters intermediate the low and high physiologic parameters.

38. The method, as set forth in claim 37, wherein the step of defining the rate zone detection threshold signal to be a prescribed function of the physiologic parameter for physiologic parameters intermediate the low and high physiologic parameters comprises:
   defining the rate zone detection threshold signal to assume a linear relationship relative to the sensed physiologic parameter.

39. The method, as set forth in claim 37, wherein the step of defining the rate zone detection threshold signal to be a prescribed function of the physiologic parameter or physiologic parameters intermediate the low and high physiologic parameters comprises:
   defining the rate zone detection threshold signal to assume a stair-step relationship relative to the sensed physiologic parameter.

* * * * *